(12) United States Patent
Tice

(10) Patent No.: US 7,301,640 B2
(45) Date of Patent: Nov. 27, 2007

(54) SYSTEM AND METHOD OF CONDENSATION REDUCTION IN AN ELECTRICAL UNIT

(75) Inventor: Lee D. Tice, Bartlett, IL (US)

(73) Assignee: Honeywell International, Inc., Morristown, NJ (US)

( * ) Notice: Subject to any disclaimer, the term of this patent is extended or adjusted under 35 U.S.C. 154(b) by 191 days.

(21) Appl. No.: 11/018,625

(22) Filed: Dec. 21, 2004

(65) Prior Publication Data

US 2006/0139647 A1 Jun. 29, 2006

(51) Int. Cl.
*G01N 21/61* (2006.01)

(52) U.S. Cl. .................................... 356/437; 250/343

(58) Field of Classification Search ........ 356/437–438; 250/343

See application file for complete search history.

(56) References Cited

U.S. PATENT DOCUMENTS

| 4,749,276 | A  | * | 6/1988 | Bragg et al. ........... 356/440 |
| 4,826,327 | A  | * | 5/1989 | Michell ................ 374/20 |
| 6,191,421 | B1 | * | 2/2001 | Yamamori et al. ...... 250/343 |
| 2003/0091089 | A1 | * | 5/2003 | Krausse .............. 374/16 |

* cited by examiner

*Primary Examiner*—Richard A. Rosenberger
(74) *Attorney, Agent, or Firm*—Welsh & Katz, Ltd.

(57) ABSTRACT

A non-dispersive infra-red gas detector includes a condensation eliminating heater. The heater can be intermittently energized in response to a signal received from an environmental sensor. Signals from a gas sensor in the detector can be processed to determine when to energize the heater.

8 Claims, 4 Drawing Sheets

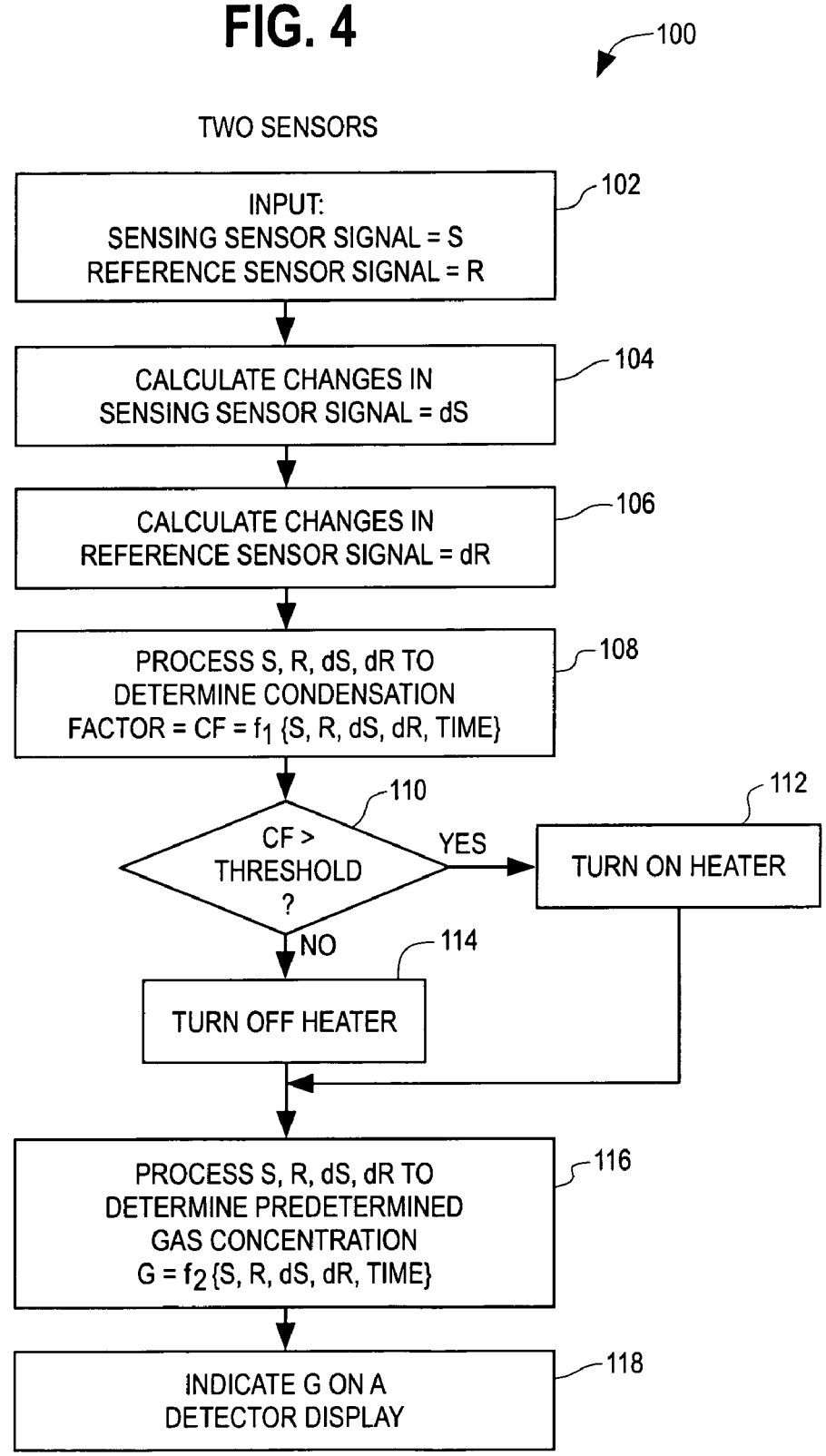

SYSTEM AND METHOD OF CONDENSATION REDUCTION IN AN ELECTRICAL UNIT

FIELD OF THE INVENTION

The invention pertains to ambient condition detectors which include condensation susceptible optical elements. More particularly, the invention pertains to gas detectors which include at least one optical element.

BACKGROUND OF THE INVENTION

Various types of known gas and smoke detectors incorporate optical elements. These could include lenses or reflectors, which are used to direct or focus light relative to a sensing element, for example, a photo diode or other form of opto/electrical converter. Such optical components are recognized as being useful and appropriate in that they can provide improved performance and reduced size in such detectors. However, they are susceptible to airborne water vapor which can condense on and deteriorate their performance.

It is recognized that condensation can occur on optical surfaces which are colder relative to warmer incoming humidity carrying ambient air. The difference in temperature results in the airborne water vapor condensing on the optical surfaces.

In many instances, the condensation is particularly likely to occur if the detector is carried from a colder environmental condition to a warmer environmental condition. This is especially an issue if the warmer ambient air is higher in humidity.

It has been known to continually heat optical surfaces in such detectors to maintain their temperature above the dew point. In known detectors, the heating process is carried out continuously. This requires, of course, supplying a certain amount of electrical energy continuously to the detector only for the purpose of heating the respective optical components.

There continues to be a need for detectors which require lower average power, while still carrying out an appropriate heating function of relevant optical components, then now available. Additionally, it would be desirable to be able to improve battery life and to decrease the power requirements of any wiring which is used to interconnect pluralities of detectors with a common power supply and a remote system. Preferably such improved operating efficiency could be achieved without substantially increasing component costs, manufacturing costs, or complexity of such detectors.

BRIEF DESCRIPTION OF THE DRAWINGS

FIG. 4 is a flow diagram illustrating a method of signal processing in accordance with the invention.

DETAILED DESCRIPTION OF THE EMBODIMENTS

Figure 1:
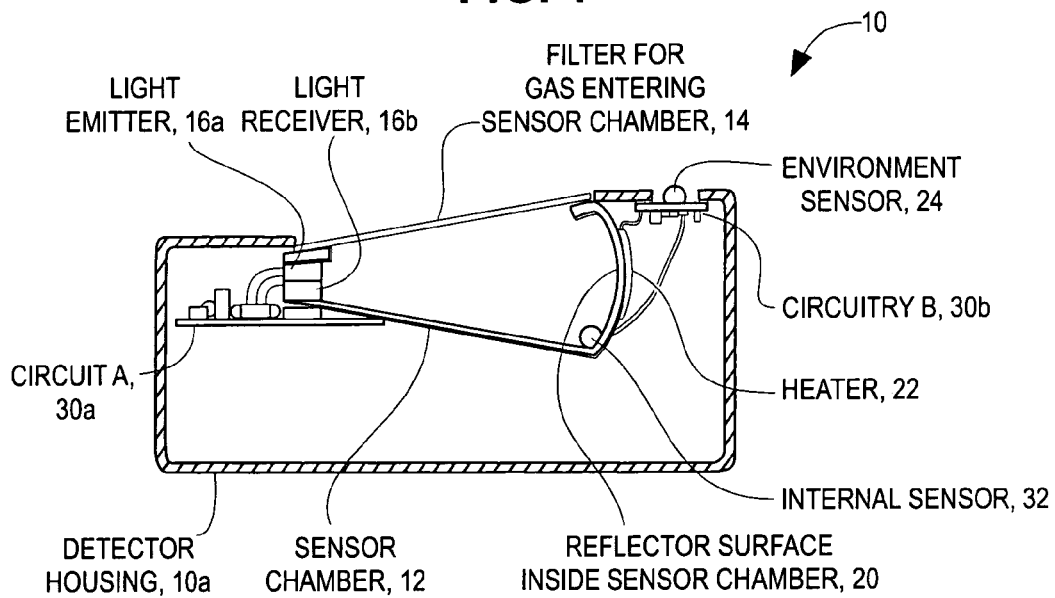
FIG. 1 is a side sectional view of a detector in accordance with the invention.

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

In a disclosed embodiment, an NDIR (non-dispersive IR) detector contains a sensor chamber which is enclosed in a detector housing. The sensor chamber has an air entry portion that can be closed with a gas permeable filter to keep contaminants out of the sensing chamber.

The sensing chamber has a radiant energy, or, light emitter at one end that emits light towards the reflector at the opposite end of the chamber. The light emitter emits an initial intensity of light frequency that is absorbed by the gas being sensed. The reflector focuses the reflected light to a receiver located near the emitter. The intensity of the received light with the gas is compared with the intensity without the gas to determine the gas concentration.

In one embodiment, the light will travel the length of the sensing chamber twice to increase the absorption characteristics of the gas being sensed. The light emitter and light receiver are connected to circuit that provides the drive and sensing circuitry. This circuitry analyzes the light receiver signals and determines the gas concentration.

A chamber as described above has been disclosed in U.S. patent application Ser. No. 10/627,361 filed Jul. 25, 2003 and entitled "Chamber for Gas Detector" and assigned to the Assignee hereof. That application is hereby incorporated herein by reference.

The detector also contains circuitry that is used, at least in part, to control a heater in or adjacent to the sensing chamber such that it will heat the reflector when power is applied to the heater. At least one environmental sensor can be used to sense a predetermined characteristic of the environment. The sensor is connected to circuitry that can control the heater as a function of that characteristic. The environmental sensor may be one of a class of temperature sensor, humidity sensor, condensation sensor, or another type of sensor that provides information that can be used to assess the potential for condensation to occur on the reflector.

At least one internal sensor may optionally be used to sense an internal characteristic of the sensing chamber. The internal sensor may be one of a class of temperature sensor, humidity sensor, condensation sensor, or another type of sensor that provides information that can be used to assess the potential for condensation to occur on the reflector.

When the environmental sensor and associated circuit determines that a predetermine characteristic is present, the circuit will turn ON a voltage drive to the heater such it warms up and thus warms up the reflector. When the circuit determines that reflector has been warmed to a predetermined temperature relative to the environmental, the circuit will turn OFF the voltage drive to the heater at conserve power.

The power is turned ON to the heater only during environmental conditions that may cause condensation to occur on the reflector and then only for limited time. Thus the average power requirements for heating the reflector to prevent condensation is very low for most of the time. This is heating on demand as a function of the environment sensing.

In another aspect, the detector may also contain an internal sensor to sense a condition of the chamber to provide additional information to the circuit to determine the time that the voltage drive should be applied to the heater. This internal sensor signal can provide feedback on the temperature of the chamber to the circuit. The internal sensor represents a source of additional information to assess the condensation potential.

In one embodiment, the environmental sensor is a temperature sensor and the internal sensor is a temperature sensor. In this case, the control circuits monitor the environmental sensor to determine the temperature and changes in temperature. The circuit also monitors the internal sensor to determine that temperature and changes in temperature. When the environmental temperature and internal temperatures are within predetermined relationships, it can be determined that condensation will not occur.

One such circumstance occurs when the detector is carried from a warm environment to a cold environment and the environment sensor detects a rapid decrease in temperature while the internal sensor is detecting a slow decrease in temperature. Another circumstance occurs where the detector is carried from a warm environment to a very warm environment and the temperatures from the environmental sensor and internal sensors indicate that the reflector will remain above a reasonable dew point such that condensation will not occur. When the environmental sensor signals and internal sensor signals are such that condensation is possible, then the circuit will apply power to the heater to warm the reflector during the transient condition.

In another embodiment, the environmental sensor can be implemented as a condensation sensor. Since this sensor is essentially external of the sensing chamber, it will respond first to environmental conditions such that power can be applied to the heater to warm the reflector before condensation occurs on the reflector. An internal sensor may be used and be implemented as a condensation sensor to detect the potential for condensation on the reflector.

In yet another embodiment, two light receivers can be used in the detector. The first light receiver functions as a gas sensing receiver and has a light filter that passes the light frequencies that are absorbed by the sensed gas. The second light receiver functions as a reference receiver that has a light filter that does not contain the light frequencies absorbed by the sensed gas. The signal from the second light receiver thus acts as a reference for altering the information obtained from the first light receiver.

In another aspect of the invention, the reflector will have two portions. One reflects a part of the light from the light emitter to the sensing receiver. Another reflects a part of the light from the light emitter to the reference receiver.

When condensation occurs on these portions of the reflector, the signal received at each of the receivers will decrease. A decreasing signal from the reference sensor is not normal. It can be indicative of condensation. That decrease in signal can be used to make an adjustment to the signal from the sensing sensor prior to carrying out gas concentration processing. In addition, the control circuit attached to the light receivers can process the signal sensor output and reference sensor output to determine when to apply power to the heater to warm the reflector. The reflector can be heated for a predetermined time period or until sensed conditions return to normal.

The control circuit of the detector can include a processor that determines the gas concentration from the sensing and reference signals. The relationship of the sensing and reference signals is dependent upon condensation and variations in the electrical components. For example, if the light out of the light emitter decreases by 10%, then both the sensing and reference signals will decrease by 10%. This may be interpreted initially as a condensation condition so the circuits will turn the heater on.

If the heater is turned on and the sensing and reference signals remain unchanged after a predetermined period of time, then the circuit may conclude there is no condensation and turn the heater off. The circuit can then use the reference signals in a ratio-metric method to compensate the sensing signal for determining the gas concentration. The power into the heater can be monitored to determine that the heater is functioning properly. An internal sensor can also be used to assess that the heater is functioning properly and determine the chamber temperature.

In another aspect of the invention, where a gas membrane is used with a gas sensing chamber, the inflow rate of ambient air is decreased. Hence, there can be a time interval before the condensation accumulates to a level to affect sensor operation. Signals from a non-gas sensor can predictably trigger heating of the optical element prior to condensation accumulation to thereby halt the condensation process.

There are other combinations of an environmental sensor, internal sensor, sensing signals, and reference signal to control a heater intermittently. Embodiments of this invention turn a heater ON and OFF to conserve average power and extend the life of any battery that may be associated with the detector. They also decrease power requirements of wiring attached to the detector.

Figure 1A:
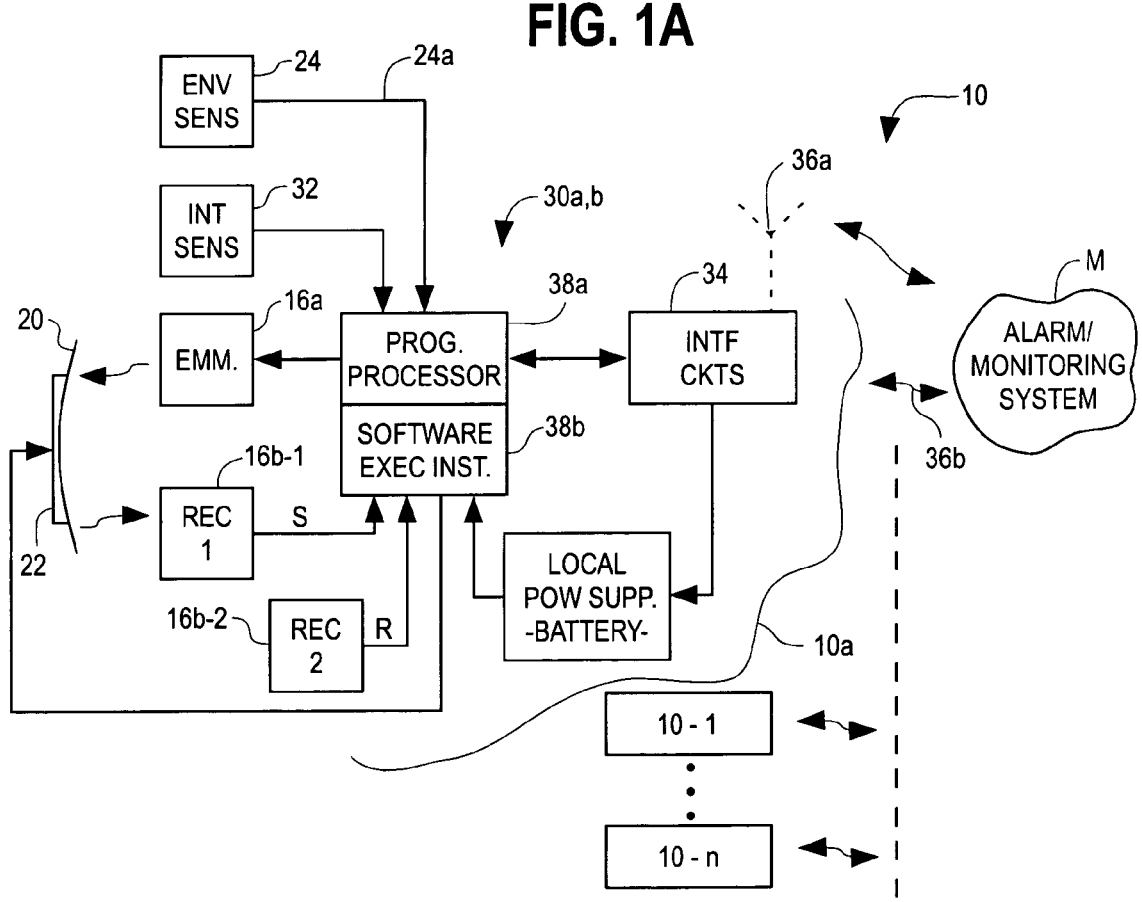
FIG. 1A is a block diagram of the detector of FIG. 1 illustrating additional characteristics thereof.

FIGS. 1, 1A illustrate a detector 10 in accordance with the present invention. It will be understood that detector 10 is exemplary only and reflective of the best mode of practicing the invention. However, the invention is not limited to gas detectors.

The invention is useful in electrical units which incorporate optical components of all types. Representative alternate examples include smoke detectors, as well as optical scanners where condensation is an issue.

The detector 10 incorporates a gas sensing chamber 12 configured for an inflow of ambient gas carrying atmosphere. Inflow to chamber 12 can, optionally, be through a filter 14 which is designed to permit the inflow of a selected gas, while excluding others. Those of skill in the art will understand that filter 14 is not a limitation of the present invention.

Sensing chamber 12 incorporates respectively an emitter of radiant energy, for example, a laser diode and the like 16a and one or more respective receivers 16b-1, -2. The chamber 12 as well as the emitter 16a and receivers 16b-1, -2 can be configured as described in application Ser. No. 10/627,361 filed Jul. 25, 2003, entitled "Chamber for Gas Detector" and incorporated herein by reference.

Sensing chamber 12 also includes a reflector surface 20 which receives and reflects beams of light from emitter 16a to receivers 16b-1, -2 through the gas carrying atmosphere within the chamber 12.

A heater 22 is coupled to the reflective surface 20. The heater 22 could be attached to the surface 20 or it could be integrally formed therewith. The heater 22 will increase the temperature of the reflector so that it is above the dew point to eliminate condensation on or to keep condensation from forming on the reflector surface 20.

Detector 10 also incorporates an environmental sensor 24 configured to sense an exterior ambient condition such as temperature, humidity, condensation or the like, all without limitation. Control circuitry 30, illustrated in FIG. 1 having components 30a, 30b is present in detector 10 for purposes of appropriately energizing emitter 16a, receiving signals from receivers 16b-1, -2, and, at least in part, making a determination of gas concentration in the chamber 12 as would be understood by those of skill in the art. The circuitry 30*b*, which might be coupled to the circuitry 30*a*, receives a signal through environmental sensor 24, and can energize heater 22 as needed.

Detector 10 can also incorporate an optional internal sensor 32 which is located in the chamber 12. Sensor 32 can be responsive to ambient temperature, humidity, condensation or any other condition which can be used to assess the potential for condensation to occur on the reflector 20. FIG. 1A is a block diagram illustrative of various components of the detector 10. In FIGS. 1, 1A, the same identification numerals are used for common elements.

Detector 10 also incorporates interface circuitry 34 which enables it to communicate either wirelessly, 36*a*, or via cables 36*b* with a displaced alarm/monitoring system M. A plurality of detectors 10-1 . . . 10-*n* corresponding to detector 10 can also be in communication with system M.

The control circuitry 30*a*, 30*b*, could in a preferred mode, be implemented with a programmable processor 38*a* and software 38*b* which might be in the form of executable instructions.

In summary, a first sensor senses light reflected off of the reflector and provides a first signal indicative of a predetermined gas in the sensing chamber. A second sensor senses reflected light from the reflector and provides a second signal not indicative of a predetermined gas, the second signal is different than the first signal. The control circuitry, which might include the programmed processor and associated software, receive the first and second signals and process them. The control circuitry causes power to be dissipated in the heater intermittently, dependent on the results of processing the signals. The control circuitry, at least in part determines the presence of the predetermined gas. Alternately, a third sensor can provide a third signal not indicative of a predetermined gas. The control circuitry processes at least the second signal and the third signal. In addition to causing power to be intermittently dissipated in the heater in response to the results of the processing, the control circuitry, at least in part, determines the presence of the predetermined gas.

Figure 2:
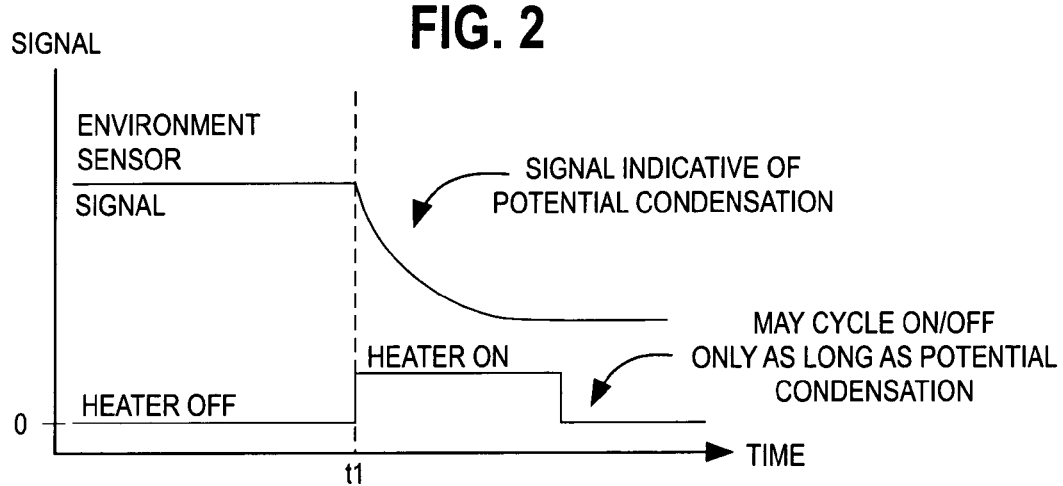
FIG. 2 illustrates one form of signal processing in accordance with the invention.

FIG. 2 illustrates one operational mode of the detector 10 in minimizing condensation problems relative to an optical element, such as the element 20. As illustrated in FIG. 2, where the environmental sensor 24 emits a signal which starting at time t1 is indicative of the presence of potential condensation due to, for example, high humidity, that signal can be coupled via line 24*a* to the control circuitry 30. When the signal on the line 24*a* indicates potential condensation, the control circuitry 30 can intermittently energize the heater 22, also as illustrated on FIG. 2, until a determination has been made that the condensation problem has been obviated.

For example, the control circuitry 30 could determine that the heater 22 has been effective in warming reflector 20 to a predetermined temperature relative to the environment. In this instance, the control circuitry 30 could terminate energizing heater 22 to conserve power. Heater 22 could be energized for a preset time interval.

For example, and without limitation, the internal sensor 32 could be implemented as a thermal or temperature sensor to provide feedback to control circuitry 30 as to the temperature of the chamber. Alternately, a thermal sensor could be coupled to the reflector 20 thereby providing additional feedback as to the temperature thereof.

Since the control circuitry 30 only energizes the heater 22 at times that might cause condensation to occur on the reflector 20, average power requirements for heating the reflector to prevent condensation are very low, most of the time. Heating on demand is thus a function of the local environment and sensed conditions at the detector 10.

Figure 3A:
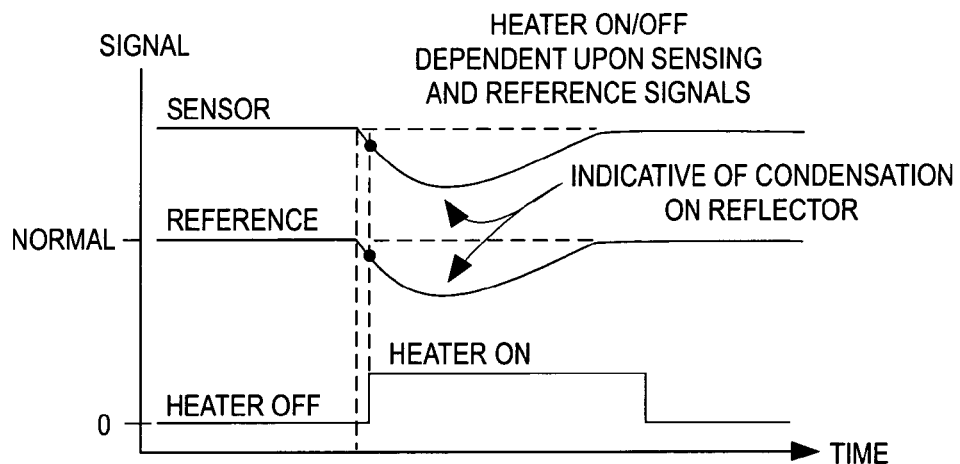
FIGS. 3A and 3B taken together illustrate a second form of signal processing in accordance with the invention.
Figure 3B:
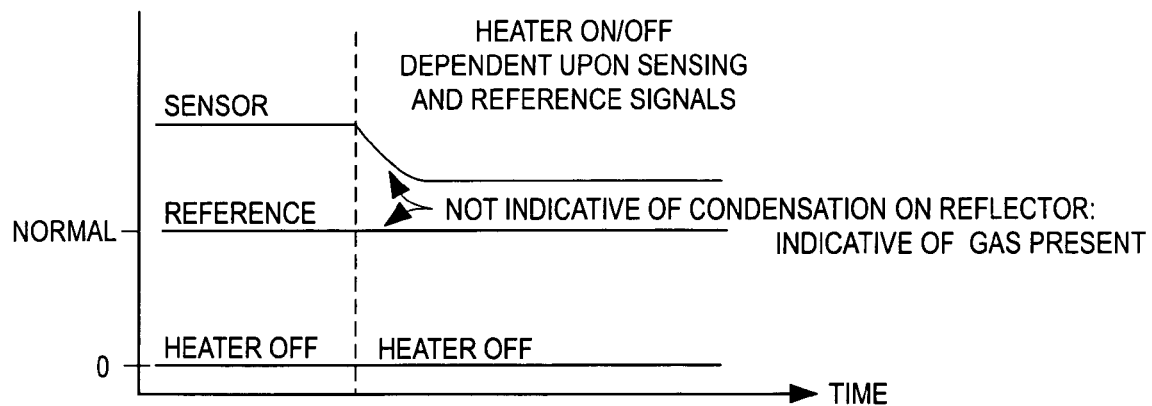

FIGS. 3A and 3B illustrate alternate operational methodologies of the detector 10. As described in the '361 application incorporated herein by reference, the chamber 12 can incorporate first and second receivers, 16*b*-1, 16*b*-2. One of them, such as 16*b*-1, operates as a gas sensing receiver. It has associated with it a filter which transmits those frequencies of light that are absorbed by the sensed gas. The second receiver 16*b*-2 is a reference receiver. It has a light filter that does not transmit the frequencies absorbed by the sensed gas. Signals from the sensor 16*b*-1, -2 can be processed in control circuitry 30 to determine a gas concentration in the chamber 12.

Reflector 20, in this embodiment, will have two regions. On region reflects a portion of light from the emitter to the sensing receiver 16*b*-1. Another reflects a portion of the light from the emitter to the reference receiver 16*b*-2. When condensation occurs on these portions of the reflector 20, the respective signal received at each of the receivers 16*b*-1, -2, will decrease.

As illustrated in FIG. 3A, a decrease in received signals from both the sensing receiver 16*b*-1 and reference receiver 16*b*-2, can be indicative of condensation on the reflector 20. At this time, the control circuitry 30 can energize the heater 22, as illustrated in FIG. 3A. Since the ouput from the two sensors 16*b*-1 and 16*b*-2, as illustrated in FIG. 3A, are changing simultaneously, the control circuitry 30 can compensate the sensing signal, from receiver 16*b*-1 with the reference signal received from 16*b*-2 as taught in the '361 Application. Alternately, control circuitry 30 can cease responding to signals received from receiver 16*b*-1 until the reference signal, received from receiver 16*b*-2, returns to normal, to avoid false positives relative to the gas of interest.

Representative time intervals for the heater 22 to clear condensation from the reflector 20 might be on the order of 30 seconds or less. Subsequent to this time interval, the control circuitry 30 could again initiate evaluating the gas concentration using the signals from the receivers 16*b*-1, -2.

As illustrated in FIG. 3B, in another embodiment, the reference signal from receiver 16*b*-2 has not changed despite the fact that the signal from the gas sensor 16*b*-1 has dropped. This is a condition which is not indicative of condensation. In this instance, the control circuitry 30 does not energize the heater 22.

FIG. 4 is a flow diagram illustrating exemplary processing by circuitry 30 using outputs from the two sensors 16*b*-1, -2. It will be understood that processing 100 is exemplary only and other forms of processing come within the spirit and scope of the present invention.

In an initial step 102, sensor and reference signals from the receivers 16*b*-1, *b*-2 are acquired by control circuitry 30. In a step 104 a differential value indicative of a change in the sensor signal from receiver 16*b*-1 is determined. In a step 106 a similar change in the reference sensor signal 16*b*-2 is also determined.

In step 108, a condensation factor CF is determined as a function of the signals received in step 102 as well as the determined incremental changes in steps 104 and 106. In a step 110, if the condensation factor exceeds a predetermined threshold, heater 22 is energized in a step 112. If not, the heater 22 is disabled in a step 114.

The same set of signals can be processed as would be understood by those of skill in the art to establish a gas concentration in the chamber 12, step 116. Finally, if desired, the gas concentration can be displayed, step 118, wherever desired, including on the respective detector as well as at the monitoring system M. Those of skill will understand that the process 100 can be periodically repeated.

Figure 5:
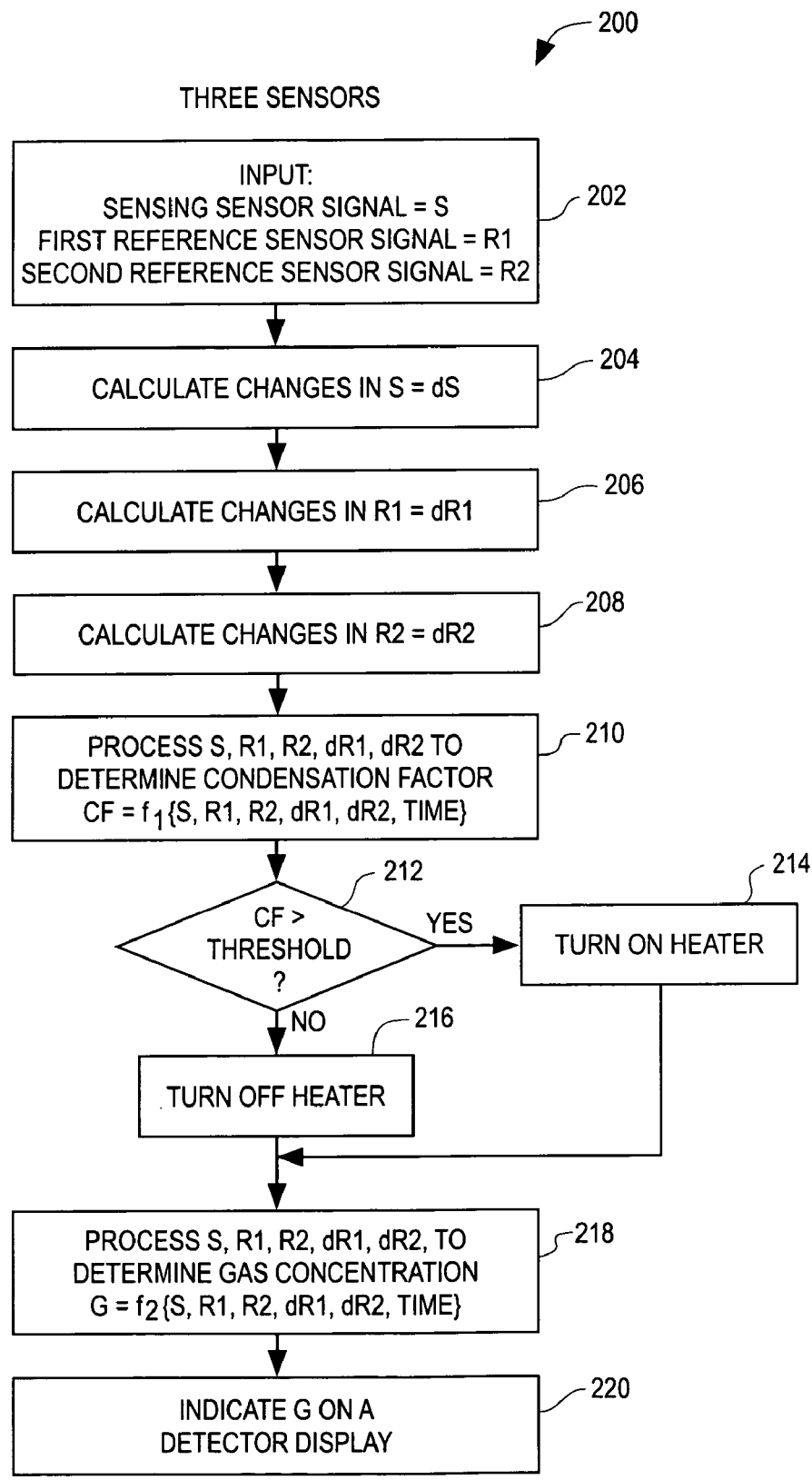
FIG. 5 is an alternate method of processing signals in accordance with the invention.

FIG. 5 is a flow diagram of an alternate method of processing 200. In FIG. 5, outputs from three sensors can be processed to establish a condensation factor as well as a gas concentration as would be understood by those of skill in the art. In a step 202, the various signal values are acquired by control circuitry 30. In steps 204, 206 and 208, incremental changes can be determined for each of the acquired signals.

In a step 210 the signal values as well as respective incremental changes can be processed to establish a condensation factor CF. That factor CF is compared to a predetermined threshold in step 212. If it exceeds the threshold value, the heater 22 is energized, step 214, otherwise the heater is turned off, step 216.

In step 218, the acquired signals as well as their incremental changes can be processed as would be understood by those of skill in the art to determine concentration of the predetermined gas in the chamber 12. Finally, in step 220, gas concentration can be displayed, optionally, at the detector or at the monitoring system M.

In summary, control circuitry 30 can determine gas concentration from the sensing and reference signals. The relationship between the sensing and reference signals will vary depending on the condensation as well as variations in the respective electrical components. If the radiant energy or light emitted by the emitter 16a decreases by 10%, for example, than both the sensing and reference signals from receivers 16b-1, -2, will decrease a similar amount. Control circuitry 30 could respond to this change as indicative of a condensation condition, in which case the heater 22 could be energized for a predetermined period of time. If in response therto, the signal levels remain unchanged, the heater 22 could be turned off in view of the fact that a condensation problem is probably not being sensed. Gas concentration processing can be resumed.

Electrical power supplied to the heater 22 could also be monitored to determine if the heater is functioning properly. The internal sensor 32 can also be used to provide information as to whether the heater is functioning properly as reflected by the temperature of the chamber 12.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A gas detector for sensing a predetermined gas comprising:
    a processor and associated circuitry;
    a sensing chamber into which at least a selected gas from an external environment can flow;
    a light emitter;
    a reflector that reflects light from the light emitter and has a heater which is at least one of attached to, or, part of the reflector wherein the heater is electrically connected to the processor and associated circuitry;
    a first sensor that senses reflected light from the reflector and provides a first signal indicative of a predetermined gas in the sensing chamber;
    a second sensor, the second sensor senses light reflected from the reflector and provides a second signal not indicative of a predetermined gas, the second signal is responsive, at least in part, to condensation on the reflector, the processor and associated circuitry receive the first signal and second signal;
    a sensor of the external environment which provides a third signal indicative thereof;
    the processor includes software that processes the first signal, the second signal, and the third signal and responsive thereto, the processor causes power to be dissipated in the heater intermittently, in response to at least the second signal, to minimize condensation on the reflector, and, the processor, in response to at least the first and second signals, determines the presence of the predetermined gas.

2. A gas detector as in claim 1 wherein the processor causes power to be dissipated in the heater when the processor determines that condensation on the reflector is likely to occur or has occurred.

3. A gas detector as in claim 1 wherein the processor indicates the presence of the predetermined gas.

4. A gas detector as in claim 1 wherein the processor indicates the concentration of the predetermined gas.

5. A gas detector for sensing a predetermined gas comprising:
    control circuitry;
    a sensing chamber into which at least a selected gas from the environment can flow;
    an emitter of radiant energy;
    a reflector that reflects light from the light emitter and has a heater associated therewith, the heater is electrically connected to the control circuitry;
    a first sensor, in the chamber, that senses radiant energy reflected from the reflector and provides a first signal indicative of a predetermined gas;
    a second sensor, in the chamber, where the second sensor senses light reflected from the reflector and which provides a second signal not indicative of a predetermined gas;
    the control circuitry including executable programs that process the first signal, second signal; and
    wherein power is intermittently dissipated in the heater dependent upon the processing of the first signal and second signal, to minimize condensation on the reflector, and where the control circuitry also determines the presence of the predetermined gas from the first and second signals.

6. A gas detector as in claim 5 which includes a third sensor which is one of a condensation sensor, a temperature sensor, or, a humidity sensor.

7. A gas detector as in claim 6 where the control circuitry responds to the three sensors to determine a condensation factor and responds thereto, to activate the heater.

8. A gas detector as in claim 7 where the control circuitry compares the condensation factor to a predetermined threshold.

* * * * *